United States Patent [19]
James

[11] Patent Number: 5,207,662
[45] Date of Patent: May 4, 1993

[54] FLUSHABLE OR DISPOSABLE DIAPER PAD WITH REUSABLE WRAP

[76] Inventor: Annett James, 755 Yale Rd., Boulder, Colo. 80303

[21] Appl. No.: 931,569

[22] Filed: Aug. 17, 1992

Related U.S. Application Data

[63] Continuation-in-part of Ser. No. 783,135, Oct. 28, 1991, abandoned.

[51] Int. Cl.[5] .................. A61F 13/62; A61F 13/76
[52] U.S. Cl. .................... 604/385.2; 604/364; 604/385.1; 604/387; 604/391; 604/394; 604/397
[58] Field of Search .............. 604/364, 386, 387, 391, 604/392, 393, 397, 385.1, 394, 389, 385.2, 358

[56] References Cited

U.S. PATENT DOCUMENTS

| | | | |
|---|---|---|---|
| 1,971,671 | 8/1934 | Alsop | 604/397 |
| 2,366,440 | 1/1945 | Clifford | 604/394 |
| 2,544,726 | 3/1951 | Rogatz | 604/401 X |
| 2,854,979 | 10/1958 | Turner et al. | 604/397 X |
| 3,636,952 | 1/1972 | George | 604/364 |
| 3,658,064 | 4/1972 | Pociluyko | 604/364 |
| 3,667,466 | 6/1972 | Ralph | 604/397 X |
| 3,693,621 | 9/1972 | Jarusik et al. | 604/397 X |
| 3,881,487 | 5/1975 | Schrading | 604/364 X |
| 4,022,210 | 5/1977 | Glassman | 604/394 |
| 4,662,877 | 5/1987 | Williams | 604/385.2 |
| 4,701,175 | 10/1987 | Boland et al. | 604/385.2 |
| 4,704,117 | 11/1987 | Mitchell | 604/391 |
| 4,773,906 | 9/1988 | Krushel | 604/391 |
| 4,808,176 | 2/1989 | Kielpikowski | 604/386 X |
| 4,892,598 | 1/1990 | Stevens et al. | 604/385.1 X |
| 5,049,145 | 9/1991 | Flug | 604/385.1 X |
| 5,137,526 | 8/1992 | Coates | 604/385.1 X |

FOREIGN PATENT DOCUMENTS

| | | | |
|---|---|---|---|
| 0475702 | 3/1992 | European Pat. Off. | 604/391 |
| 1428572 | 3/1976 | United Kingdom . | |

Primary Examiner—Randall L. Green
Assistant Examiner—Mary Beth O. Jones

[57] ABSTRACT

An improved infant and toddler diaper comprising a symmetrical anatomical pad designed to facilitate disposal by flushing and a reusable garment for use therewith, the pad having an absorbent dam and parallel longitudinal lines of perforation. The two fabric, anatomically shaped, and reusable garment having a waterproof dual strand elasticized fence of same shape around inside border for retaining all edges of pad, the waterproof fabric separates and extends at crotch and leg regions where the edges house multi and parallel strands of elastic thread.

5 Claims, 6 Drawing Sheets

FLUSHABLE OR DISPOSABLE DIAPER PAD WITH REUSABLE WRAP

This is a continuation-in-part of Ser. No. 783,135, filed Oct. 28, 1991, now abandoned.

BACKGROUND OF THE INVENTION

This invention relates to a two part diaper design system. Design Part 1, a flushable or throw away inner liner without plastic or laminate backing, and Part 2, a reusable outer wrap specifically designed to encompass Part 1.

Combination disposable and reusable diapers are prevalent in the art, however no one has developed this concept into a complete garment that is a marketable option for the diaper consumer. Disposable diapers currently available are meeting many of the consumer needs. These diapers offer efficiency and are basically effective. They do not address the consumer's desire for an effective diaper that produces less waste. As environmental concerns continue to grow, many consumers welcome alternative diapers. However, they do not wish to sacrifice function, aesthetic, or price.

In this invention, a particular system has been incorporated to bridge the gaps between functional, environmental, and aestethic concerns. Design Part 1, the inner pad is comprised of two non-woven sheets, a top and a bottom; a tissue layer placed directly under top non-woven sheet, fluff pulp and super-absorbent polymer mix, hereto referred to as moisture absorbent filler.

This symmetrical anatomical shaped pad has opposite concave sides from center at legs, thus allowing for a slender, narrowed crotch region. Extra moisture absorbent filler mix has been concentrated around, but slightly inside, the borders of this pad to form an hour glass shaped dam, thus leaving some absorption capabilities on the outside perimeter of the dam. The floor depth and wall height of this dam are visible, its primary purpose is leakage containment and absorption. The wall of this dam is positioned next to the wearer's skin and functions as a first barrier against leakage not absorbed by the dam's floor. The wall maintains a consistent width combined with the softness of the moisture absorbent filler as not to imprint the wearer's skin. This design also decreases the need for gender specific diapers. Regardless of the original point of wetness contact, the wall will provide resistance to its flow. This wall also removes a significant portion of the pad's surface area away from constant contact with the skin, thus reducing the amount of moisture trapped therein, which is readily associated with skin irritations.

The above pad description is an improvement of Prior Art cited in Pociluyko, U.S. Pat. No. 3,658,064 and Glassman U.S. Pat. No. 4,022,210. They both disclose a diaper pad insert of rectangular shape. These pads in and of themselves do not allow for liquid containment not absorbed by its core. The pad then becomes entirely dependent upon the outer garment to prevent leakage into outer clothing. The lack of body contouring in these pads causes occlusion and a bulky crotch region which becomes more undesirable as infants gain mobility. In Stevens, et al. U.S. Pat. No. 4,892,598, consideration has been given to pooling of liquid in its pad. However, the perimeter is of liquid-impermeable material and provides no absorption for liquid forced over its boundaries, containment then becomes the function of the outer wrap. The art adhered to in this pad is not intended for flushing. This invention seeks to offer consumers the flushable option. If the diaper pad is not flushed in a conventional sanitary toilet system, it may be placed in the garbage thus speeding biodegrading time because there is no plastic backing. When flushing is chosen, the pad is easily torn into three equal parts along the two parallel longitudinal lines of perforation. Additional non-woven fabric has been extended past the moisture absorbent filler at waist region so that handling or tearing does not expose hands to fecal matter. By using lines of perforation with less adhesive and no plastic, when torn the entire pad is conveniently flushed not requiring two steps as taught by Schrading in U.S. Pat. No. 3,881,487. George in U.S. Pat. No. 3,636,952 and Comerford et. al. employ a flushing technique, however they require the "stripping off" of the fluid impermeable material. This process is time consuming and the protective portion must be disposed of.

Design Part 2, the outer reusable wrap is comprised of two pattern pieces. The inner waterproof fabric and an outer cotton fabric having the same dimension at front and back waist regions where the two are attached by sewing. This feature along with elastic bands at legs and rear waist are consistent with commercially available diaper wraps. In designing this wrap detailed attention has been applied to the crotch and leg areas. To achieve maximum effectiveness and comfort, the outer and the inner fabrics are unattached in this region, with the inner waterproof fabric being cut slightly wider and housing appropriately distanced multi parallel strands of elastic thread encased by a thin 100% nylon sheer bias. The outer fabric maintains its narrowed crotch and receives a single elastic band housed by the fabric itself. The mentioned design is an improvement over wraps that employs an elliptical configuration that is sewn at the concave edge sides of the legs as described by Taniguchi in British Patent No. 1,428,572. A fencing method of attaching pad to diaper holder has been chosen in this invention. The fence is of a narrow height and constructed of the same waterproof fabric comprised in the wrap. It is attached by sewing one side completely around, but approximately one inch inside of the waterproof pattern piece having essentially the same shape thereof. The unattached edge is elasticized by sewing two appropriately distanced parallel lines of elastic thread. Again this thread is encased but before mentioned nylon bias. When pad is placed inside the fence, it is forced to maintain its integrity about the wearer's body. The elasticized fence becomes another barrier to leakage. The height of the fence is short enough to allow for speedy disassembling; it also increases the surface area of the absorbent pad, thus decreasing contact between the waterproof fabric and the wearer's skin. This is an improvement to the Prior Art of Pociluyko, U.S. Pat. No. 3,658,064. Many methods of attaching and positioning absorbent pads to outer holders are known, although not necessarily similar to present invention. Stevens et. al. U.S. Pat. No. 4,892,598 boasts a slot-forming method, Clifford U.S. Pat. No. 2,366,440 uses braces, Jarusik et. al. U.S. Pat. No. 3,693,621 employs a stem and Rogaty U.S. Pat. No. 2,544,726 uses snaps. All of these methods are cumbersome and or time consuming. In this invention, the front and the rear of this wrap is symmetrical. This symmetry in shape was found to provide the best fit, which is a desire of many diaper consumers. In most commercially available diaper wraps, the rear is elongated or somehow wider than the wraps front. These features seem excessive and bulky. The Registered Trade Mark of VELCRO has been employed as a fastening system. The hook portion of said fastening system has been cut to form approximately 2×2 inch tabs, to which previously referred, and cotton fabric is sewn on the rears of said tab. These tabs are sewn on opposite sides of the wraps rear. The pile portion of their fastening system, having a perimeter of approximately 3×2 inch, is sewn slightly in from edge and approximately three-quarters inch down from each side of wraps front. The wraps is elasticized between the pile by a three-quarter inch width elastic band having appropriate length. Wraps rear is also elasticized by three-quarter inch width elastic of longer length. Man commercially available diaper wraps employing this fastening system the pile extend the entire width of wraps front. This does allow for size adjustments but can be achieved with a small quantity as discussed above. The excess adds to cost and is bulky.

SUMMARY OF THE INVENTION

According to this invention an interdependent infant and toddler diapering system has been evoked. This invention develops a viable product to bridge the gaps between environmental waste concerns and the consumers need for a relatively low cost, less work but overall effective diaper. The inner absorbent hour glass shaped pad, though designed specifically to be housed by its wrap, has many merits of its own. This pad is composed mostly of moisture absorbent fillers Flushing is facilitated when the low strength low adhesive nonwoven casing is torn apart via the perforated longitudinal breaks, thus allowing the inner core to become disengaged. The pad is now in small pieces that can be flushed without difficulty o stoppage. A moisture absorbent wall of smaller dimensions strategically integrated about the pad to form a dam, having substantially the same shape as the pad.

The outer wrap of vertical and horizontal symmetry comprises a waterproof fabric and an exterior cotton fabric; where in these fabric at sewn together, except at the leg and crotch region. At this region the fabrics are separated, the waterproof fabric extends beyond the cotton fabric and housed strands of elastic thread encased by lightweight nylon bias. The use of multi strand elastic allows for added leakage control plus assures a comfortable snug fit. The outer fabric receives a single elastic band encased by the fabric itself completing this region. The waterproof fabric is also used to build a fence about the wraps interior to attach the inner absorbent pad. The unmounted fence's end houses two spaced elastic threads encased by nylon bias. This elastic has enough tension to keep the pad properly positioned and contain leakage but loose enough for speedy removable and insertion at changing. Both the front and the rear of wrap contain an elastic band that aids in the garments overall fit. The wrap employs an adjustable VELCRO closure system. Tabs that house the hook portion of this system is attached to the rear edge of the garment and the pile portion is attached at the front. This complete diapering system addresses most areas of concern functional, aesthetical and waste concerns voiced by the consumer. Also taught by this invention is a smaller, more effective diaper whose manufacture requires less but standard equipment known in the industry. This invention demonstrates uniformity and design simplicity, thus keeping labor intensity to a minimum. By achieving such, diaper consumers are provided an extremely effective diapering system at a palatable cost.

DETAILED DESCRIPTION OF THE PREFERRED EMBODIMENTS

Figure 1:
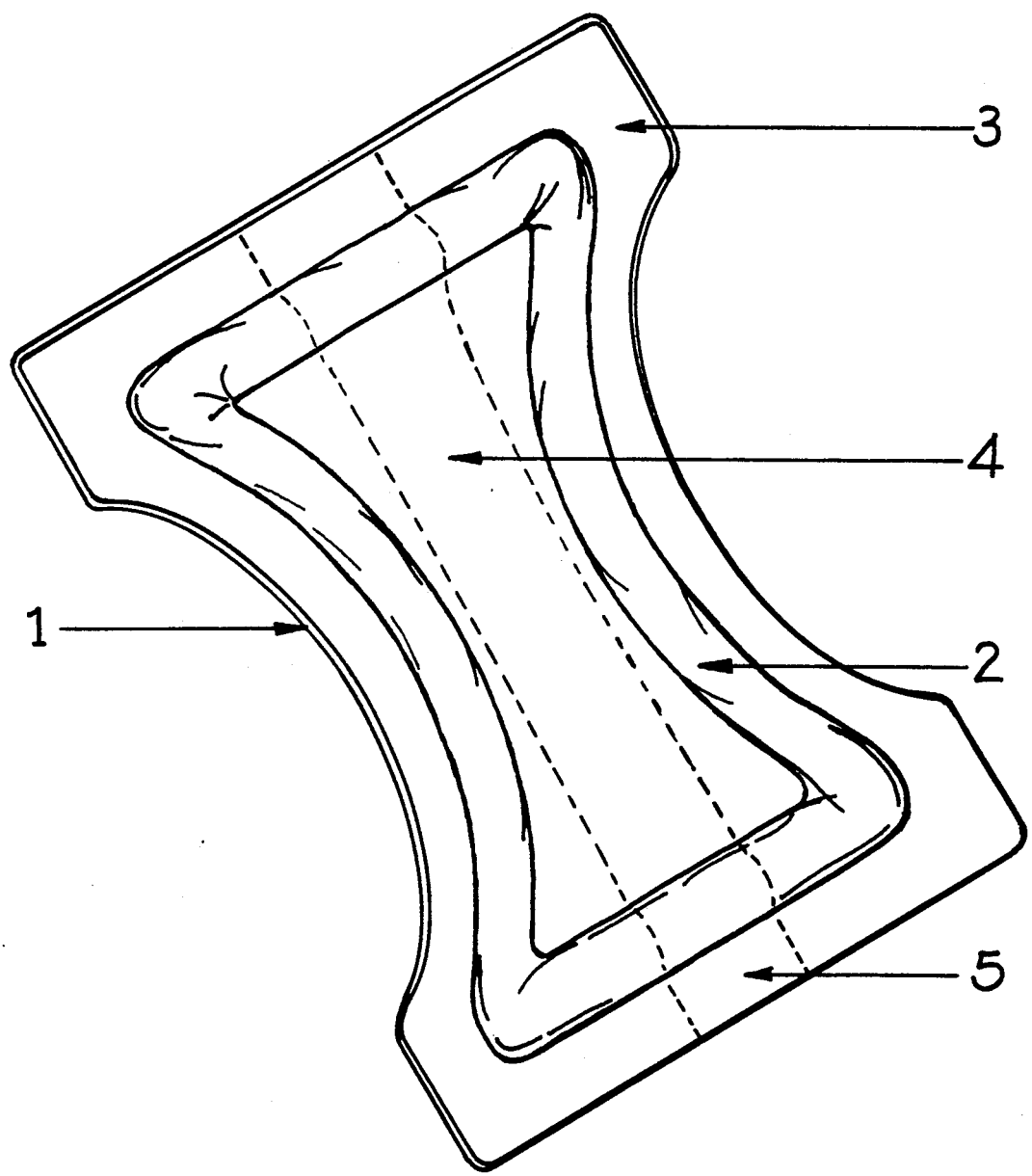
FIG. 1 is a perspective view of the inner liner.
Figure 2:
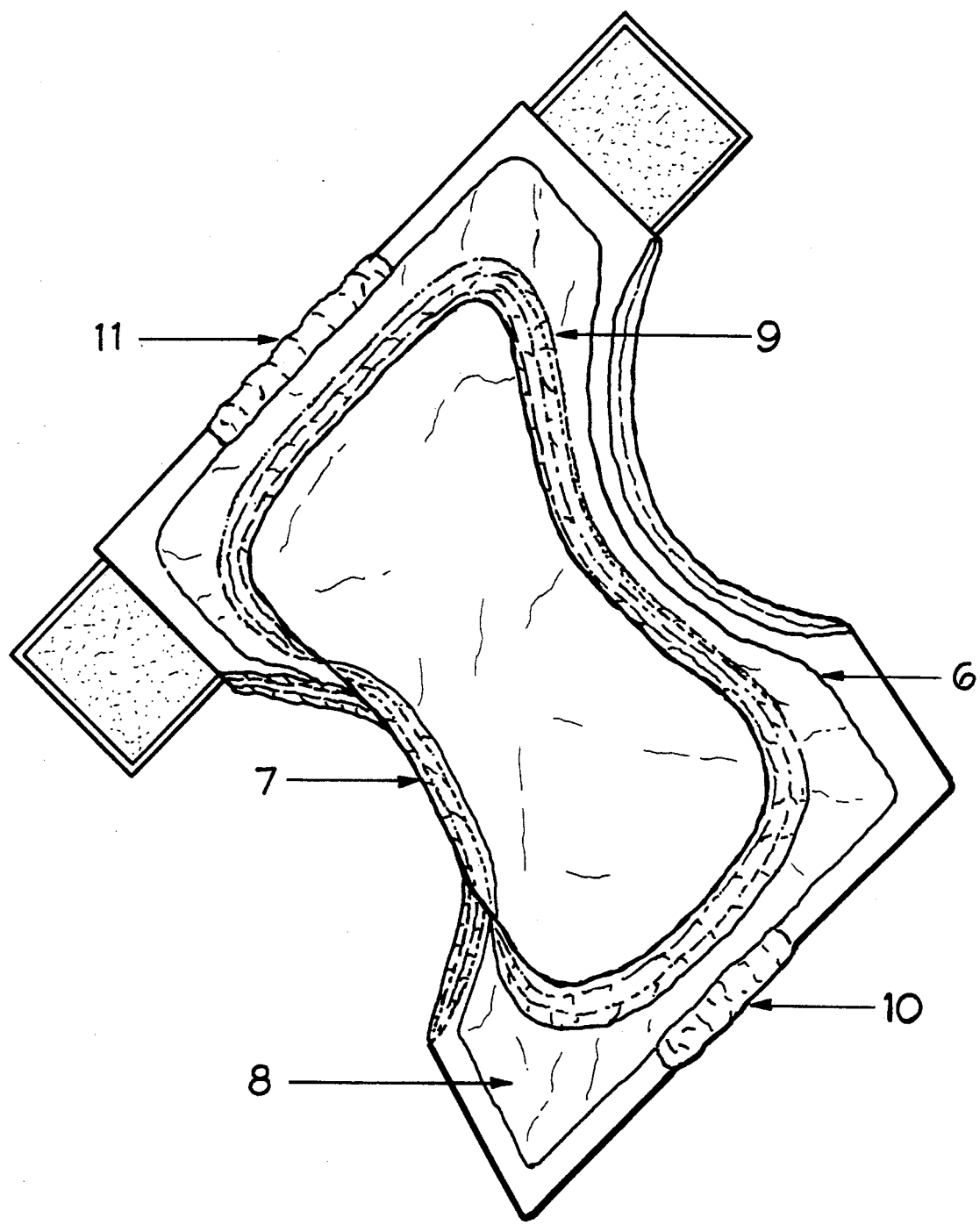
FIG. 2 is a stretched out inside view of the outer warp.

According to this invention, there is an absorbent anatomically shaped lined indicated at FIG. 1. Referring exclusively to FIG. 1, 1 shows the thickness of the absorbent filler throughout the entire line, 2 shows the wall of the anatomically shaped dam, the wall of same absorbent filler as 1 concentrated to for a visible height, this wall serves as a barrier to moisture migration, 4 created by forming 2 and shows the depth, the thickness of 4 being equal to the thickness of 1, by moving 2 inwardly of the pad center extended 1 to the border and absorbs spill over from 2 shown at 3. 2 prevents 3 and 4 from having immediate contact with the wearer's skin, thus increasing air circulation. The low-strength non woven casing that houses FIG. 1 is perforated longitudinal shown at 5. Referring to FIG. 2 showing the interior of the outer wrap stretched out, 6 is the stitched boundary attaching the fence to the garment placed inwardly from the centers approximately one inch just beneath the elastic bands of 10 front and 11 rear, 8 is the waterproof fabric comprising the fence and is the same fabric as FIG. 3, 12 having a height of approximately one inch, 7 shows the properly spaced dual parallel strands of elastic threads around the unattached end of 8, 9 refers to the extremely lightweight nylon fabric covering 7 shown in FIG. 6; providing the attachment means for FIG. 1.

Figure 3:
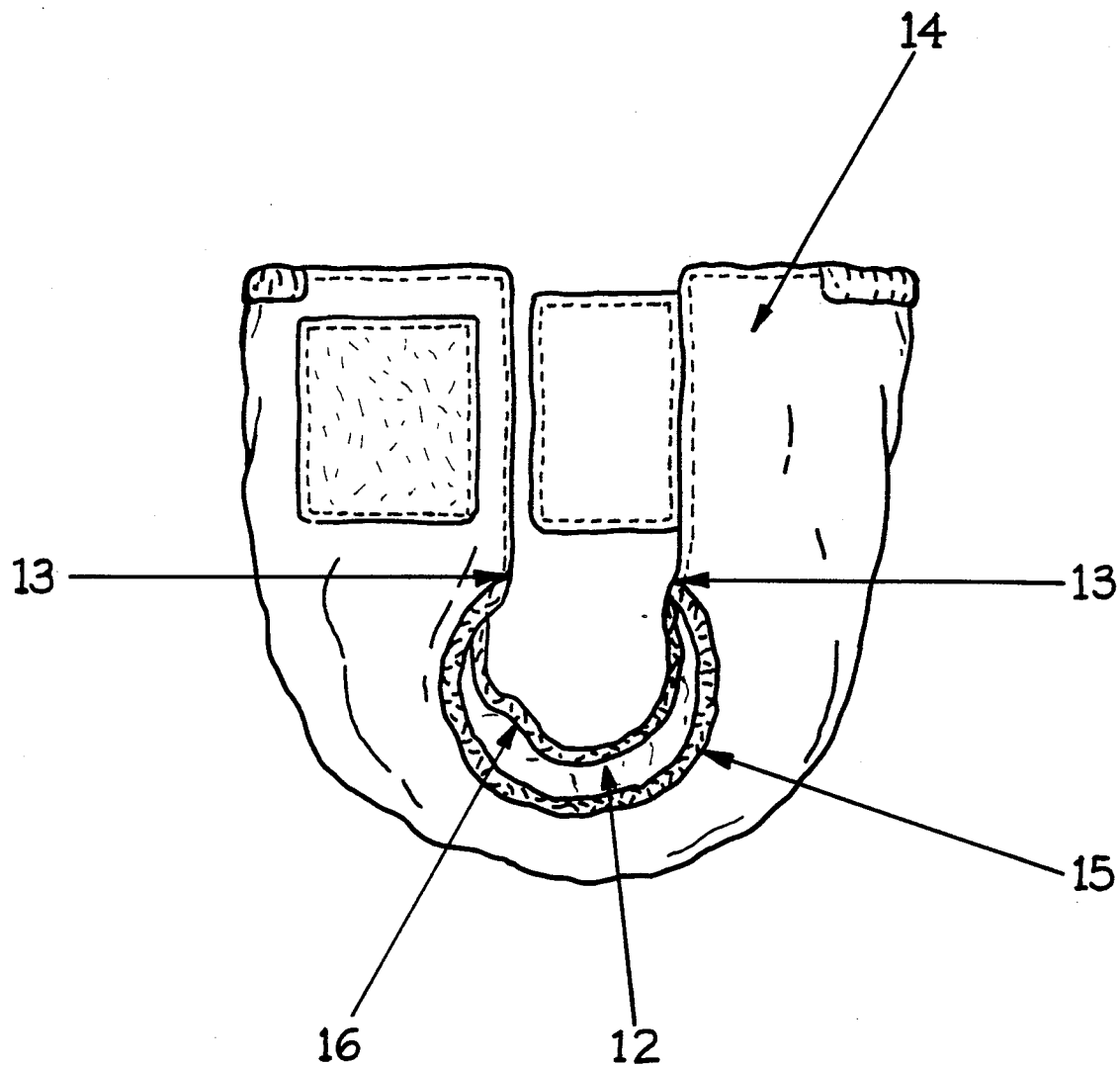
FIG. 3 is and open side view of the outer wrap encompassing leg and crotch region.
Figure 4:
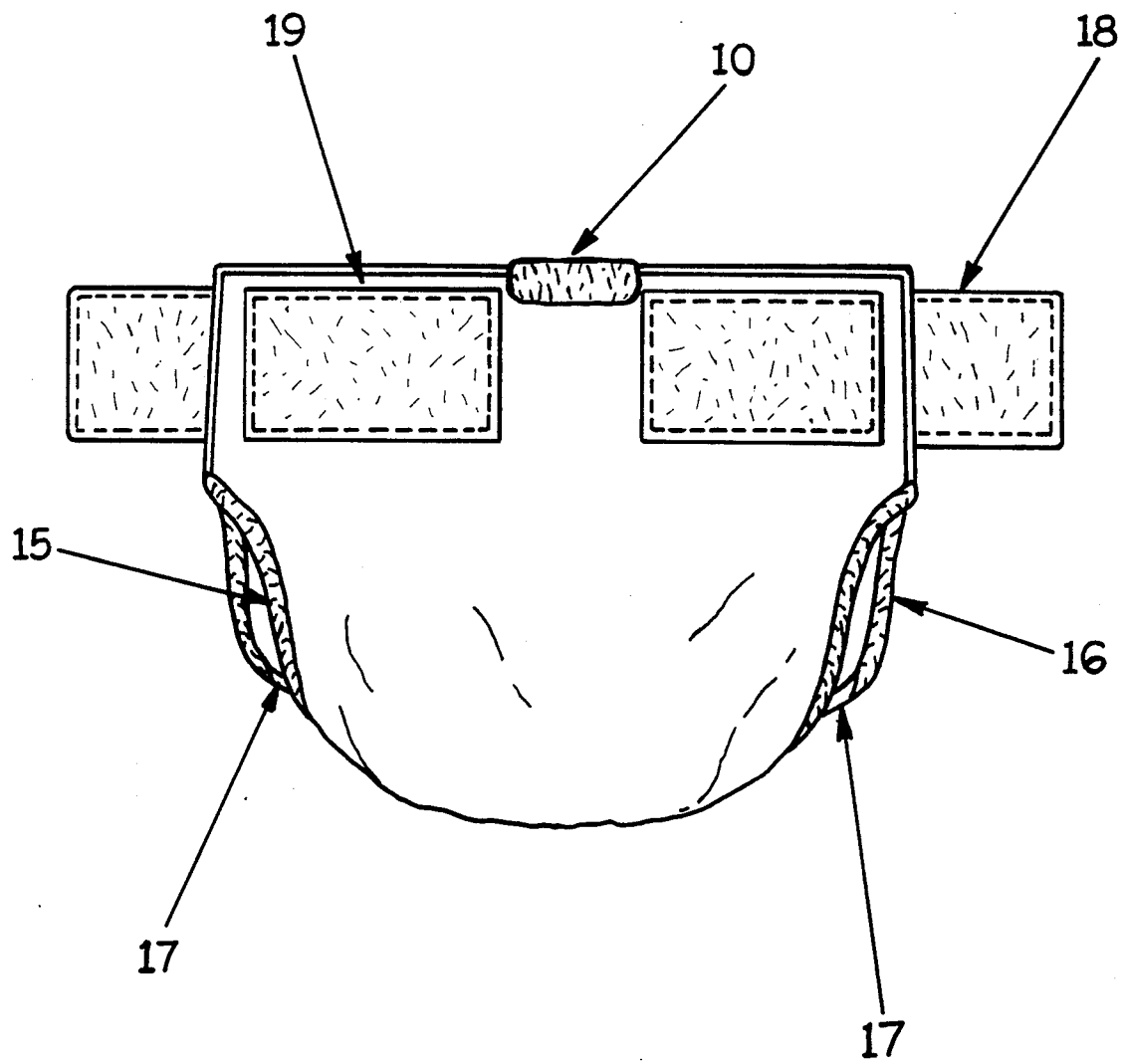
FIG. 4 is a front view of the outer wrap folded longitudinal at center.
Figure 6:
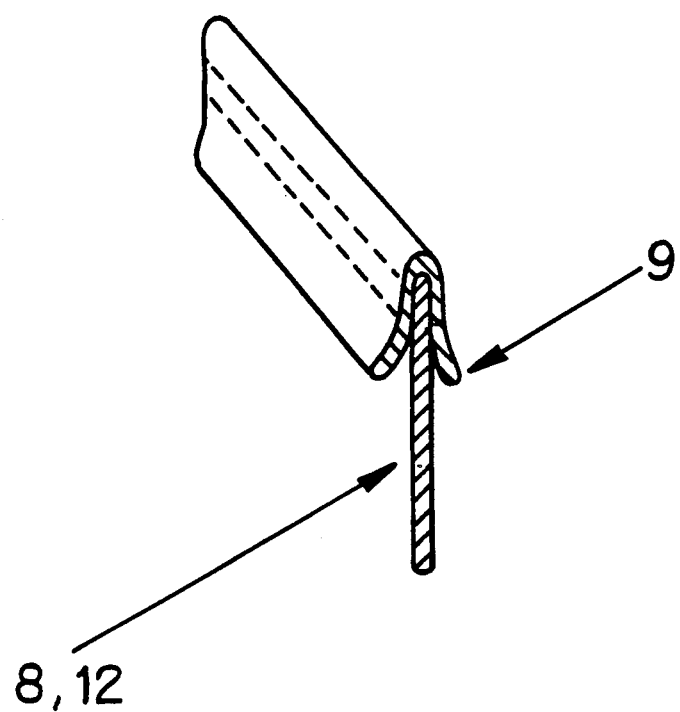
FIG. 6 is a side view of the elastic thread covering.

Referring predominately to FIG. 3 an open side view of the outer wrap with focus on the leg and crotch regions, the waterproof fabric at 12 and the exterior cotton fabric at 14 are separated at 13, the edges of 12 comprises multi parallel strands of elastic threads shown at 16, 16 is covered by nylon fabric covering shown in FIG. 6, the outer fabric 14 turned under at 13 and encompasses a one-fourth inch width single elastic band shown at 15 referring to FIGS. 3 and 4 the separation of the fabrics 12 and 14 occurs at point 13 wherein 12 extends beyond 14 shown at 17, 18, and 19 shows the means for securing the diaper about the wearer.

Figure 5:
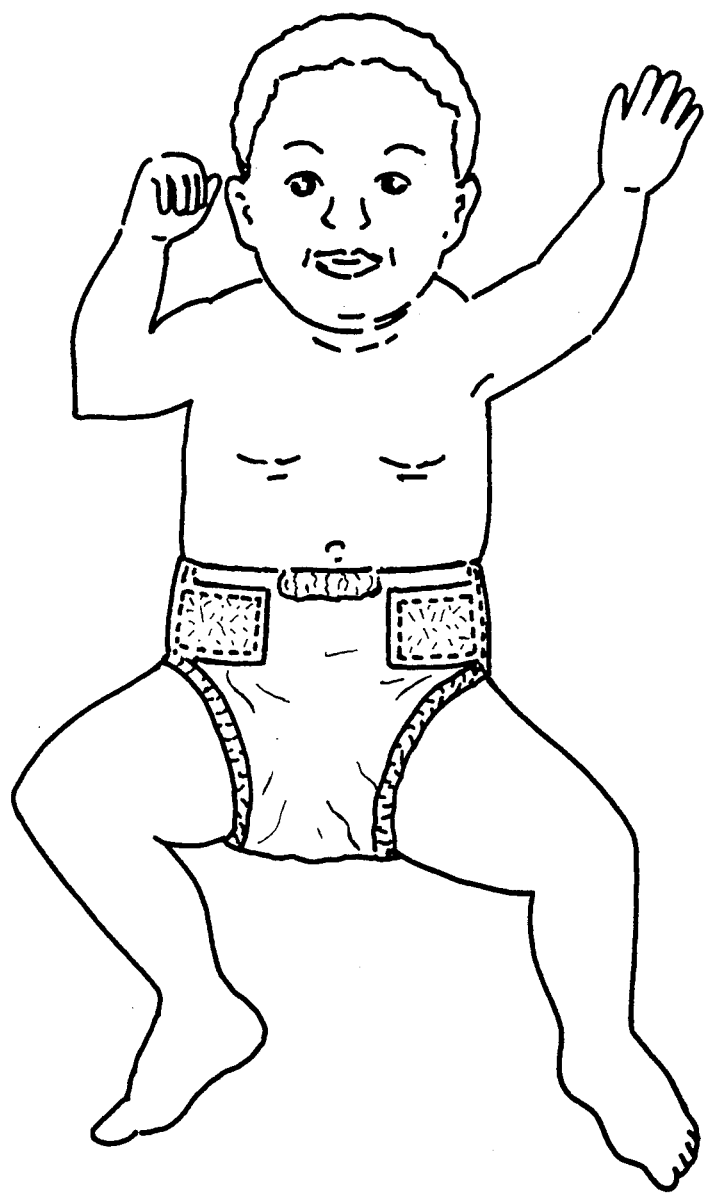
FIG. 5 is a front view of this invention of an infant.

Referring to FIG. 5, the diaper is positioned about the wearer, wherein 20 shows the snug fit created by extending the waterproof fabric 12 and adding multi parallel strands of elastic thread 16, the narrow elastic band 15 adds to the garment fit and appearance. FIG. 6 is a side view of the edges of the waterproof fabric 8 and 12 with the light weigh nylon fabric attached covering the parallel lines of elastic threads 7 and 16.

What is claimed is:

1. A diaper comprising:
   a. an exterior washable and reusable wrap having a front waist, a rear waist, a center portion disposed therebetween and a periphery defined by side edges, said wrap including an inner waterproof layer and an outer layer comprising cotton;

b. an interior liner having a front waist portion, a rear waist portion, a center portion disposed therebetween, and a periphery defined by side edges, said liner being disposable and flushable and having a moisture absorbent filler therein;

c. said wrap including means for attaching said liner to said wrap, said means for attaching said liner comprising an upstanding fence having a top, a base and a height, said fence being space along the length of the side edges of said wrap, the base of said fence being stitched to said inner layer of said wrap slightly inwardly of the side edges of said wrap, the top of said fence being elasticized by dual parallel lines of elastic threads and being spaced in a direction towards said wearer approximately one inch from said inner layer, said fence forming a pocket for housing the side edges of said liner;

d. said absorbent liner including an upstanding dam containing absorbent material, said dam being spaced inside the side edges of said liner to prevent moisture from migrating outwardly to the side edges of said liner; and e. said absorbent liner including a plurality of spaced perforated lines defining areas of weakness, said perforated lines intersecting said absorbent dam.

2. The diaper as described in claim 1 wherein said inner and outer layers of said liner are unattached at the portions of the side edge of the liner which are proximal to the crotch and legs.

3. The diaper as described in claim 2 wherein said waterproof layer extends beyond said outer layer at at the portions of the side edge of the liner which are proximal to the crotch and legs.

4. The diaper as described in claim 3 wherein said waterproof layer includes multi parallel strands of elastic thread at the portions of the side edge of the liner which are proximal to the crotch and legs.

5. The diaper as described in either claim 1 or claim 4 wherein said elastic threads includes a 100% nylon sheer fabric covering.

* * * * *